(12) United States Patent
Grothaus et al.

(10) Patent No.: US 6,569,636 B2
(45) Date of Patent: May 27, 2003

(54) ASSAY FOR MODULATORS OF METALLO-ENZYME ACTIVITY

(75) Inventors: Paul G. Grothaus, Mililani, HI (US); Dana E. Davis, San Jose, CA (US); Sean O'Malley, Honolulu, HI (US)

(73) Assignee: Hawaii Biotechnology Group, Inc., Aiea, HI (US)

( * ) Notice: Subject to any disclaimer, the term of this patent is extended or adjusted under 35 U.S.C. 154(b) by 0 days.

(21) Appl. No.: 09/320,893

(22) Filed: May 27, 1999

(65) Prior Publication Data

US 2001/0046663 A1 Nov. 29, 2001

Related U.S. Application Data

(60) Provisional application No. 60/087,456, filed on Jun. 1, 1998, and provisional application No. 60/087,124, filed on May 29, 1998.

(51) Int. Cl.[7] .................. G01N 33/543; C12Q 1/37; C12N 9/50; A61K 38/00; C07D 401/00
(52) U.S. Cl. .................. 435/7.92; 435/4; 435/23; 435/24; 435/183; 435/212; 435/215; 435/217; 435/218; 435/219; 435/DIG. 14; 530/300; 530/333; 546/201; 548/495; 560/41; 560/169; 560/312; 562/623
(58) Field of Search .................. 562/623; 560/41, 560/312, 169; 548/495; 546/201; 435/4, 23, 24, 212, 215, 217, 218, 219, 183, 975, 970, 968; 570/300, 333, 827

(56) References Cited

U.S. PATENT DOCUMENTS 5,073,483 A * 12/1991 Lebacq .................. 435/6
5,183,900 A * 2/1993 Galardy et al. .................. 548/495
5,288,514 A * 2/1994 Ellman .................. 427/2
5,639,746 A * 6/1997 Yelm .................. 514/210
5,672,598 A * 9/1997 De et al. .................. 514/212
5,677,282 A   10/1997 Oleksyszyn et al.
5,811,252 A * 9/1998 Verheijen .................. 435/23

FOREIGN PATENT DOCUMENTS

| WO | WO 96/26223 | 8/1996 | |
| WO | WO 96/26918 | 9/1996 | |
| WO | WO 97/40065 | 10/1997 | |
| WO | WO 98/08933 | 3/1998 | |
| WO | WO 98/18754 | * 5/1998 | ......... C07C/259/06 |
| WO | WO 99/06555 | 2/1999 | |

OTHER PUBLICATIONS

Chen et al., "Biased Combinatorial Libraries: Novel Ligands for the SH3 Domain of Phosphatidylinositol 3–Kinase," Science, 115, p. 12591–1259.2, 1993.*

Fodor et al., "Light Directed, Spatially Addressable Parallel Chemical Synthesis," Science, 251, pp. 767–773, 1991.*

Cotton, F. and Wilkinson, G., Advanced Inorganic Chemistry, 5th Ed., Chapter 30: "Bioinorganic Chemistry," John Wiley & Sons: New York, pp. 1335–1336, 1988.*

* cited by examiner

Primary Examiner—Maurie Baker
(74) Attorney, Agent, or Firm—Morrison & Foerster LLP

(57) ABSTRACT

An assay is disclosed for determining whether a test compound modulates the activity of an enzyme having a metallated active site. The assay method employs a comparison of the binding ability of the metallated and unmetallated forms of the enzyme to the test compound.

13 Claims, 1 Drawing Sheet

ASSAY FOR MODULATORS OF METALLO-ENZYME ACTIVITY

RELATED APPLICATIONS

The present application claims the benefit of U.S. Provisional Application No. 60/087,456 filed Jun. 1, 1998 and U.S. Provisional Application No. 60/087,124 filed May 29, 1998, which are hereby incorporated by reference in its entirety, as if fully set forth.

TECHNICAL FIELD

The present invention is directed to an assay system for assessing whether a compound modulates the activity of an enzyme with a metallated active site. More precisely, the invention concerns a method whereby the compound is provided attached to a solid support and binding of an enzyme is assessed with and without the presence of metal.

BACKGROUND ART

The use of solid supported assays for binding is well known in the art. Various labeling methods are available whereby a compound bound to a solid support can be shown to be complexed therewith. Labels include fluorescent labels, dye labels, enzyme labels, and radioisotope labels. The labeling can be either direct—i.e., the compound tested for binding to a ligand attached to a solid support may itself be labeled, or a secondary labeling event can be employed—e.g., a bound antibody may be detected by a labeled antibody from another species. Such means of detection are well understood.

The present invention takes advantage of these mechanisms to determine whether a compound will modulate the activity of an enzyme wherein the enzyme has a metallated active site. This is accomplished by testing the binding of the enzyme to immobilized compounds both with and without the presence of metal.

DISCLOSURE OF THE INVENTION

In one aspect, the invention is directed to a method to determine whether a test compound modulates the activity of an enzyme that has a metallated active site, which method comprises:

a) providing said test compound coupled to a solid support;

b) treating said solid support with the enzyme in metallated form;

c) determining as a positive result of b) that the enzyme binds to said solid support and as a negative result of b) that said enzyme does not bind to said solid support;

d) treating said solid support with said enzyme in a nonmetallated form;

e) determining as a positive result of d) that the enzyme binds to said solid support and as a negative result of d) that said enzyme does not bind to said solid support;

f) whereby a positive result in c) and a negative result in e) identifies said test compound as a modulator of said activity.

In particularly preferred embodiments, the method is used to determine whether a metalloprotease is modulated by a test compound and to ascertain a member of a library of compounds which will modulate the activity of such an enzyme.

MODES OF CARRYING OUT THE INVENTION

Figure 1:
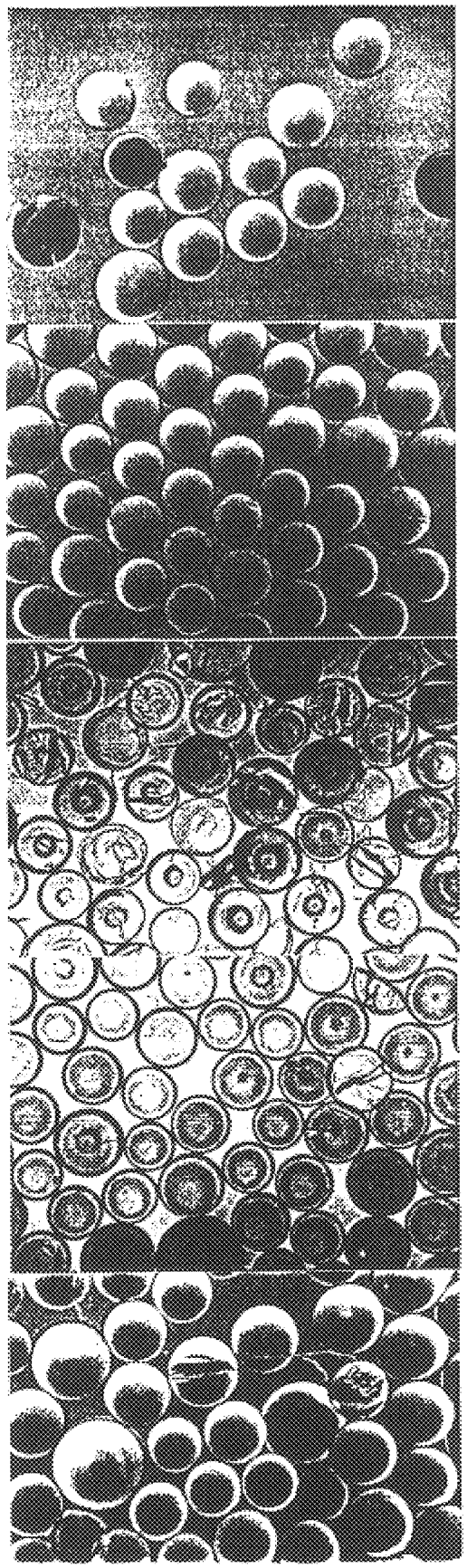
FIG. 1 is a photocopy of 100×photomicrographs of beads coated with test compounds under various conditions.

In the assay method of the invention, the compound to be tested is first coupled to solid support. Any solid support can be used, including appropriately derivatized surfaces which may have any geometric configuration, e.g., plates and blocks. However, in order to maximize the efficiency of the assay, it is desirable to derivatize the compounds to be tested on beads. A multiplicity of beads which contain a multiplicity of compounds permit more than one compound to be tested at once.

Typical beads or resins include polyvinyl, polyvinyl chloride, polystyrene, silica, carbohydrates such as sepharose or agarose and the like. A means for derivatizing beads of this nature are well known in the art.

Once the compound has been derivatized to the solid support, it is treated with a metallated enzyme, whereby the compound's ability to modulate the activity of the enzyme is to be tested. The enzyme is a metallated enzyme containing metal in the active site. This first contact is thus in the presence of metal. The binding of the enzyme to the supported compound is then detected using any suitable means. For example, the enzyme may be biotinylated and then treated with an avidin-bound dye, or using an avidin-mediated binding. Alternatively, the enzyme may be reacted with a suitable antibody which itself bears a label, including a fluorescent, dye, radioactive or enzyme label. Any suitable labeling means can be used. A label may be covalently coupled to the enzyme by means of a linker moiety.

The solid supports where binding has been demonstrated are then treated to remove metal ion, for example, by treating with a chelating agent such as EDTA. Those supports where the color is retained even in the absence of metal, contain compounds which have bound the enzyme at other than the metal-containing active site. Those solid supports where removal of the metal releases the enzyme contain compound which bind to the metallated active site.

Thus, compounds that will modulate the activity of the enzyme tested bind to the enzyme in the presence of metal, but not in its absence. Compounds that bind at irrelevant locations show similar characteristics both in the presence and absence of metal.

The method of the invention is especially useful in sorting compounds in combinatorial libraries for their modulation activities. Under these circumstances, in a convenient form of the assay, the various members of the library are bound to individual beads. When the enzyme is contacted with the library in the presence of metal ion, or in its metallated form those beads which show label may be removed and retested in the presence of an agent that removes the metal. Those beads that become unlabeled in the absence of metal contain compounds that modulate the activity of the metal-dependent enzyme.

Although it is convenient to conduct the assay as described above, it is not necessary to conduct the assay sequentially—i.e., the library may be divided into two portions and one portion tested for binding to enzyme in the presence of metal ion and the other tested in the absence of metal ion. Under such a protocol, however, an orderly array of the solid supports is required so that the results can be correlated for individual solid supports. For example, the beads may be placed in a grid so that the corresponding compounds in each case occupy the same portion of the grid or at least have a known relationship.

A large number of enzymes that contain metals in the active site are known. Particularly important are metal-containing proteases and in a preferred embodiment, modulators of these proteases can be identified using the method of the invention.

The following example is intended to illustrate but not to limit the invention.

A multiplicity of resin beads is prepared, each coupled to a peptide which has a carbobenzoxy group at the N-terminus, followed by an alanine residue, followed by an amino acid residue (X) which can represent any of 16 different amino acids, followed by a residue which is 1-amino-ethylphosphonic acid (the phosphonic acid analog of alanine) followed by an additional residue (Y) which is any of five α-hydroxy acids; followed by a residue (Z) which is any one of 16 amino acids, followed by another alanine residue, and then coupled at the C-terminus to the resin. In the compounds of the library, X and Z represent any of 16 different amino acids and Y represents any of five α-hydroxy acids. Thus, the number of compounds possible in the library is 1280 hexapeptides. The library was synthesized using the split-mix techniques on 90 μm TentaGel resin. Each resin bead displays only one peptide.

The library of beads was then contacted with Botulinum A light chain which is provided a dye label using a biotin/avidin/biotin coupling. Biotin derivatized Botulinum A light chain was prepared by alkylation of the three free cysteine residues with biotin-BMCC. Biotin-BMCC is of the formula:

Biotin-BMCC

The biotinylated enzyme is then labeled with avidin, further bound to a dye-biotin conjugate.

In the alternative, avidin itself is coupled to dyes, including gallocyanine (blue), ethyl red (red) or carminic acid (red) 5-(biotinamido)pentylamine via the standard carbodiimide/N-hydroxysuccinimide method.

The beads were tested for nonspecific binding as follows:

Biotinylated synthesis resin was treated with avidin followed by incubation with the biotin-dye conjugates described above. Acetylated synthesis resin was used as a negative control. The ethyl red conjugated biotin showed substantial nonspecific binding to the resin—i.e., it bound to the acetylated resin as well as biotinylated resin. Of the two remaining dye conjugates, the carminic acid conjugate gave the most acceptable background. It bound to the biotin/avidin-labeled beads but not to the acetylated beads.

The library of peptides coupled to beads described above was screened in three 40-mg batches corresponding to 100,000 beads in a volume of 120 μl.

The beads were first incubated with biotinylated Botulinum A light-chain, then washed, then incubated with streptavidin, then washed, then treated with dye-labeled (carminic acid) biotin.

The results are showed in panel a) of FIG. 1. Most beads were colorless but several stained a deep red. The remainder ranged from light pink to rose. About 150 of the colored beads were selected and set aside as a pool (shown in panel b) of FIG. 1). A subset of 20 of the most deeply colored beads from the first pool was selected and set aside as a second pool. Both pools were washed extensively with 100 mM glycine/1 mM EDTA, pH 2.5 until no color remained. The washed beads are shown in panel c) of FIG. 1.

The two pools of beads were then rescreened using Botulinum A light-chain protein which is biotinylated but contains no zinc ion. In the first pool, most beads remained colorless with about 30% developing a small range of light pink coloration, as shown in panel d) of FIG. 1. In the second pool, the deep red beads quickly recovered their deep red color showing nonspecific binding ((panel e) of FIG. 1).

Beads that were strongly positive in the zinc containing Botulinum A light-chain binding assay and negative in the apo-Botulinum A light-chain display ligands specific for the zinc binding site of the light chain.

What is claimed is:

1. A method to determine whether a test compound modulates the enzymatic activity of an enzyme that has an active site comprising a metal, which method comprises:
   a) providing said test compound coupled to a solid support;
   b) contacting said test compound coupled to said solid support with the enzyme in metallated form;
   c) determining as a positive result of b) that the enzyme binds to said test compound coupled to solid support and as a negative result of b) that said enzyme does not bind to said test compound coupled to solid support;

d) contacting said test compound coupled to solid support with said enzyme in a nonmetallated form;

e) determining as a positive result of d) that the enzyme binds to said test compound coupled to solid support and as a negative result of d) that said enzyme does not bind to said test compound coupled to solid support;

f) whereby a positive result in c) and a negative result in e) identifies said test compound as a compound that modulates said enzymatic activity.

2. The method of claim 1 wherein said enzyme in both metallated and nonmetallated forms is labeled with a visible dye, a fluorescent dye or a radio label and said binding is determined by assessing the presence, absence or amount of label associated with the binding of the enzyme to the test compound coupled to solid support.

3. The method of claim 2 wherein said label comprises a visible dye.

4. The method of claim 3 wherein said visible dye is gallocyanine, ethyl red, or carminic acid.

5. The method of claim 2 wherein said label is bound to said enzyme covalently through a linker moiety.

6. The method of claim 1 wherein said test compound is a member of a library of test compounds.

7. The method of claim 1 wherein said solid support comprises beads.

8. The method of claim 1 wherein said enzyme is a metalloprotease.

9. A method to determine whether a test compound modulates the enzymatic activity of a metalloprotease enzyme which method comprises:

a) providing said test compound coupled to a support which comprises beads;

b) providing said enzyme coupled to a label which is a visible colored dye;

c) incubating said beads with said enzyme wherein said enzyme is in metallated form;

d) determining as a positive result of c) that beads retain the color of the visible colored dye and as a negative result of c) that said beads do not retain the color of the visible colored dye;

e) incubating said beads with the labeled enzyme wherein said enzyme is in nonmetallated form;

f) determining as a positive result of e) that beads retain the color of the visible colored dye and as a negative result of e) that said beads do not retain the color of the visible colored dye;

g) whereby a positive result in d) and a negative result in f) identify said test compound as a compound that modulates said enzymatic activity.

10. A method to detect, in a library of compound members, a member that modulates the enzymatic activity of an enzyme that has an active site comprising a metal, which method comprises:

a) providing said library as members bound to a multiplicity of beads, each bead coupled to molecules of an individual member compound;

b) contacting beads coupled to members of said library with said enzyme in metallated form;

c) determining for a member as a positive result of b) that the enzyme binds to beads coupled to said member of the library and as a negative result of b) that said enzyme does not bind to beads coupled to said member of said library;

d) contacting at least the members of the library which give a positive result in c) with the enzyme in a nonmetallated form;

e) determining for a member as a positive result of d) that the enzyme binds to beads coupled to said member of the library and as a negative result of d) that said enzyme does not bind to beads coupled to said member of said library;

f) whereby a positive result in c) and a negative result in e) for a given member of the library, identifies that member as a member that modulates said enzymatic activity.

11. The method of claim 10 wherein steps b) and c) are performed prior to steps d) and e) so as to provide a subset of members which give positive results in step c) for testing in step d).

12. A kit for performance of the method of claim 10 kit comprises, in appropriate containers, a) a multiplicity of beads wherein each bead is coupled to molecules of a single member of a library of test compounds; and b) a metallated enzyme of interest coupled to a visible dye, a fluorescent dye or a radio label; and c) a reagent for effecting removal of metal from said metallated enzyme.

13. The kit of claim 12 wherein the label is a visible dye.

* * * * *